United States Patent
Acosta et al.

(10) Patent No.: US 8,246,676 B2
(45) Date of Patent: *Aug. 21, 2012

(54) IMPLANTABLE VENOUS VALVE

(75) Inventors: George M. Acosta, Phoenix, AZ (US); George F. Kick, Casa Grande, AZ (US)

(73) Assignee: Biomedical Research Associates, Inc., Akron, OH (US)

(*) Notice: Subject to any disclaimer, the term of this patent is extended or adjusted under 35 U.S.C. 154(b) by 971 days.

This patent is subject to a terminal disclaimer.

(21) Appl. No.: 11/217,648

(22) Filed: Sep. 1, 2005

(65) Prior Publication Data

US 2006/0247762 A1     Nov. 2, 2006

Related U.S. Application Data

(63) Continuation of application No. 10/123,649, filed on Apr. 16, 2002, now Pat. No. 6,958,076.

(60) Provisional application No. 60/284,047, filed on Apr. 16, 2001.

(51) Int. Cl.
*A61F 2/06* (2006.01)

(52) U.S. Cl. .................................................. 623/1.24

(58) Field of Classification Search ................. 623/1.11, 623/1.24, 2.12, 2.17
See application file for complete search history.

(56) References Cited

U.S. PATENT DOCUMENTS

| | | | |
|---|---|---|---|
| 3,717,883 A | 2/1973 | Mosher | |
| 4,192,020 A * | 3/1980 | Davis et al. | 623/2.19 |
| 4,253,201 A | 3/1981 | Ross et al. | |
| 4,605,407 A | 8/1986 | Black et al. | |
| 4,759,758 A | 7/1988 | Gabbay | |
| 4,759,759 A | 7/1988 | Walker et al. | |
| 4,936,317 A * | 6/1990 | MacGregor | 607/120 |
| 5,480,424 A | 1/1996 | Cox | |
| 5,500,014 A | 3/1996 | Quijano et al. | |
| 5,554,185 A | 9/1996 | Block et al. | |
| 5,562,729 A | 10/1996 | Purdy et al. | |
| 5,800,531 A * | 9/1998 | Cosgrove et al. | 623/2.11 |
| 5,824,061 A | 10/1998 | Quijano et al. | |

(Continued)

FOREIGN PATENT DOCUMENTS

WO     WO 2007/016097     2/2007

OTHER PUBLICATIONS

Dalsing et al., "A multicenter, phase I evaluation of cryopreserved venous valve . . . ," Journal of Vascular Surgery, vol. 30 #5, pp. 854-866, (1999).

(Continued)

*Primary Examiner* — William H. Matthews
(74) *Attorney, Agent, or Firm* — Fay Sharpe LLP

(57) ABSTRACT

A venous valve prosthesis includes a hollow conduit (40) defining a central passageway through which blood may flow. Opposing, pliable leaflet members (30) are located within the conduit and move back and forth between a first, open position, whereby blood may flow through the central passageway in a first direction, and a second, closed position, whereby blood is prevented from backflowing through the central passageway in a second direction which is opposite the first direction. A hollow and generally cylindrical support member (10, 20) retains the leaflet members and is coaxially disposed within the conduit. The support member includes opposing cutaway regions (18) defining two axially extending struts (16) supporting the leaflet members. The cutaway regions, in cooperation with the struts, allow the leaflet members to collapse inwardly to the closed position.

17 Claims, 13 Drawing Sheets

U.S. PATENT DOCUMENTS

| | | | |
|---|---|---|---|
| 5,861,028 A * | 1/1999 | Angell | 623/2.11 |
| 5,861,029 A * | 1/1999 | Evdokimov et al. | 623/2.26 |
| 6,029,671 A | 2/2000 | Stevens et al. | |
| 6,264,700 B1 * | 7/2001 | Kilcoyne et al. | 623/23.68 |
| 6,440,164 B1 | 8/2002 | DiMatteo et al. | |
| 6,527,800 B1 | 3/2003 | McGuckin, Jr. et al. | |
| 6,676,698 B2 | 1/2004 | McGuckin, Jr. et al. | |
| 6,682,559 B2 | 1/2004 | Myers et al. | |
| 6,958,076 B2 * | 10/2005 | Acosta et al. | 623/1.24 |

OTHER PUBLICATIONS

Kumins et al., "Free tissue transfer provides durable treatment for . . . ," Journal of Vascular Surgery, vol. 32 #5, pp. 848-854, (2000).

DeLaria et al., "Hemodynamic evaluation of a bioprosthetic venous prosthesis," Journal of Vascular Surgery, vol. 18, #4, pp. 577-586, (1993).

Hill et al., "Development of a prosthetic venous valve," Journal of Biomedical Materials Research, vol. 19, pp. 827-832, (1985).

Taheri et al., "Experimental Prosthetic Vein Valve," The American Journal of Surgery, vol. 156, pp. 111-114, (1988).

Van Cleef, "A Vein Has a Preferential Axis of Flattening," Elsevier Science Publishing Co., Inc., Dermatol Surg Oncol 19, pp. 468-470, (1993).

Taheri et al., "Experimental Prosthetic Vein Valve . . . ," The Journal of Vascular Diseases, vol. 46, #4, pp. 299-303, (1995).

Bemmelen et al., "The Mechanism of Venous Valve Closure," Arch Surg, vol. 125, pp. 617-619, (1990).

Reeves et al., "Mechanical characteristics of lyophilized human . . . ," Journal of Vascular Surgery, vol. 26, #5, pp., 823-828, (1997).

Criado et al., "Venous Disease," Curr Probl Sur., pp. 339-399, (1991).

Burkhart et al., "Experimental repair of venous valvular insufficiency . . . ," Journal of Vascular Surgery, vol. 26, #5, pp. 817-822, (1997).

Wang et al., "In vitro performance of venous valve prostheses . . . ," ASAIO J, vol. 38, #3, pp. 213-215, (1992)—Abstract.

* cited by examiner

IMPLANTABLE VENOUS VALVE

CROSS-REFERENCE TO RELATED APPLICATION

This application is a continuation of prior application Ser. No. 10/123,649, filed Apr. 16, 2002, now U.S. Pat. No. 6,958,076 which claims the benefit of U.S. Provisional Application No. 60/284,047, filed Apr. 16, 2001. Each of application Ser. No. 10/123,649 and Prov. Application No. 60/284,047 is incorporated herein by reference in its entirety.

BACKGROUND OF THE INVENTION

The present invention relates generally to vascular implants and, more particularly, to a synthetic or artificial prosthetic valve device for implantation in a blood vein. In another aspect, the present invention relates to a method for making the same. In yet another aspect, the present invention relates to a method for implanting the venous valve device of the present invention. In still another aspect, the present invention relates to a method for the treatment, reversal, and/or prevention of venous insufficiency and its consequences in animals, including humans.

Venous blood flow returns de-oxygenated blood from the distal extremities to the heart via two mechanisms. The first is the perfusion pressure resulting from the arterial blood flow through tissue to the venous circulation system. Where arterial pressure prior to perfusion may be 60 to 200 mm Hg, the resulting venous pressure is typically 10 to 40 mm Hg. The second mechanism is the calf muscle, which, when contracted, compresses the veins (tibial and peroneal) overlying the bone and, through a system of valves, directs blood flow toward the heart. This is the organized flow of blood through a normal, healthy person.

Venous valves, especially those in the upper leg, perform an important function. When a person rises from a seated to a standing position, arterial blood pressure increases instantaneously to insure adequate perfusion to the brain and other critical organs. In the legs and arms, the transit time of this increased arterial pressure is delayed, resulting in a temporary drop in venous pressure. Venous pressure drops as blood flow responds to body position change and gravity, thereby reducing the volume of blood available to the right heart and possibly reducing the flow of oxygenated blood to the brain. In such a case, a person could become light headed, dizzy or experience syncope. It is the function of valves in the iliac, femoral and, to a lesser degree, more distal vein valves to detect these drops in pressure and resulting change of direction of blood flow and to close to prevent blood from pooling in the legs to maintain blood volume in the heart and head. The valves reopen and the system returns to normal forward flow when the reflected arterial pressure again appears in the venous circulation. Compromised valves, however, would allow reverse blood flow and pooling.

Venous insufficiency is caused by compromised vein valves in the leg. Venous insufficiency is recognized in two forms: (1) chronic venous ulcer, and (2) varicose veins. In the United States, chronic venous insufficiency (CVI) associated with skin changes and ulcers effect six to seven million people. Each year, 900,000 new patients are diagnosed with this disorder while 800,000 patients suffer the consequences of active venous ulcers. Health care costs in the United States are estimated at one billion dollars with a loss of 2 million days of productivity. The costs in the western industrial countries exceed those of the United States.

Skin changes and ulcers due to venous insufficiency usually result from valve damage or deep venous occlusion following a bout of DVT. Active venous ulcers are the leading cause of leg ulceration and the long-term healing prognosis, when compared to arterial and diabetic ulcers, is poor. While estimated to be 10 times more common, chronic venous insufficiency has received less attention than arterial insufficiency. CVI is the seventh most debilitating disease in the United States. Principle risk factors associated with venous ulcers include increased age, obesity, male gender, lower extremity trauma, and a history of deep vein thrombosis (DVT).

Varicose veins, the second manifestation of chronic venous insufficiency, occur when walls of the vein lose their elasticity, causing vessel dilation that stretches the valves to incompetence. Varicose veins are estimated to affect 4.2% of the adult western population. It is also estimated that 27% of the United States adult population have some form of detectable lower extremity venous abnormality, primarily varicose veins and telangiectasia. Approximately half of this population has significant varicose veins for which treatment will be sought. Primary risk factors are a history of phlebitis, female gender, and a family history of varicose veins.

Traditional conservative therapy relies primarily on compression hosiery, such as that devised by Jobst in 1950. The goal of this therapy is to reduce symptoms while allowing patients to remain ambulatory and productive. Active venous ulcers are often treated with a combination of topical drug therapy and pressure dressing as first described by Unna in 1896. However, the prognosis of chronic venous ulcers is poor, with only 50% healing within 4 months. In most cases, the ulcer will recur at least once.

Surgical therapy, consisting of high ligation and vein stripping for varicose veins was first described by Trendelenburg in 1891 and was improved by Keller in 1905. This approach generally provides a good cosmetic result with reduction in symptoms. However, procedures that remove the saphenous vein also deprive the patient of the best conduit for cardiac and peripheral arterial reconstruction. This may bring into question the precept of leaving varicose veins alone until they become a problem. Dilated and varicose vessels are not appropriate for use as arterial conduits.

Surgeons, recognizing the value of valve restoration, have devised surgical procedures for selected patients to create, repair, and/or transplant vein valves in an effort to restore "normal" venous blood flow and heal ulcers. Patient selection and the operator are key to the success of these procedures.

Criado et al. [1] provide a good overview of venous disease including venous insufficiency and a rational for current treatment options.

In 1985, Hill et al. [2], described artificial valve prosthesis. In this experiment, Pellethane® urethane elastomer was used to fabricate a valve. A human umbilical cord valve was used for casting a valve in the Pellethane material. The valves were mounted in a stainless steel tube for implant in animal model. The fabricated valve remained patent for from 5 to 8 days. Results suggested more study was necessary to improve long-term durability.

Bemmelen et al. [3] is one of a series of reports that looks at the mechanical operating characteristics of the native human valve. The pressure and velocity measurements documented in the study, as well as the measurement methods used, provide a basic understanding of venous flow dynamics.

One cause of venous insufficiency is the loss of elasticity in the vein wall. In 1993, van Cleef [4] documented the orientation of valves and perforating vessels. The paper refers to an implantable device that, when placed parallel to the valve leaflets, will stretch the leaflets to competency. The percutaneous prosthesis consists of two stems and a leaf spring opening the stems. The device is not a valve replacement, but rather allows flattening of the vessel and, when placed parallel to the valve cusps, allows retightening of the native valve cusps. This understanding is important because an artificial valve may replace the "stretched" valve and it must accommodate the vein lumen enlargement.

In 1988, Taheri et al. [5], fabricated mechanical valves with pyrolyte carbon coated titanium and platinum. The sizes of these bileaflet valves were from 5 to 10 mm in diameter. An annular ring was provided so that a suture could be placed around the implanted device to secure position and orientation in the vessel. This valve was patterned after a bileaflet cardiac valve. This series demonstrated both patency and competency to reverse flow at 16 weeks. Two valves did occlude when they physically migrated to other anatomic locations within the venous system. No anticoagulants were used in this series. The employed valves and others are described in Taheri [6].

In 1995, Taheri et al. [7], published their long-term experience with the bileaflet valve. In this series, nine dogs were implanted with the bileaflet mechanical vein valves for up to two years. Over this period, all valves were rendered functionless because of a dense ingrowth of intimal hyperplasia.

In 1993, DeLaria et al. [8], described their in-vitro experience with a glutaraldehyde-fixed valve and metal mounting system using a venous flow simulator. The report suggests this device performs well to the parameters expected in the venous circulation. This report describes the use of a glutaraldehyde-fixed bovine jugular vein in an animal model. Tissue fixation of this type is common in heart valves. The authors note that valve failures were related to intimal hyperplasia related to tissue ingrowth at the sewing ring.

Transplants of human tissue are often considered the best replacements. In 1997, Reeves et al. [9] investigated the mechanical characteristics of lyophilized human saphenous vein valves in vitro as a potential source of valves for transplantation.

Cryopreserved human aortic valves and valved conduits are routinely used to replace cardiac valves and for cardiac outflow reconstructions. Burkhart et al. [10] describes the result of cryopreserved valved saphenous vein transplantation, specifically, the use of cryopreserved venous valve allografts in greyhounds.

Dalsing et al. [11] investigated the use of cryopreserved venous valve allograft in humans. This follow-up study suggests that the cryopreserved approach is best suited for patients without other options.

Kumins et al. [12] describe free tissue transfer for treatment of large venous ulcers, resulting in transplantation of hundreds of functioning microvenous valves, as a substitute for valveplasty. The devastation of venous ulcers has led many to find a cure without correction of the underlying circulation defects. This paper suggests a cure can be had for between $30,000 and $76,000.

Patented experimental work on prosthetic venous valves is generally focused on two groups: (1) Syde Taheri, who proposes a mechanical valve based on the St. Jude heart valve concept, and (2) the Baxter group whose venous valve is based on glutaraldehyde-fixed heart valve devices. Briefly, Taheri et al. [5, 6, 7] were the first to report a metallic vein replacement valve. This device was effective in the animal model for treating venous insufficiency. At 3 to 8 months, valve patency was demonstrated. In [7], it was reported that over a 2-year period, valve function was compromised by intimal hyperplasia. These results may be better than they appear, since the tissue ingrowth may have been controlled by an attachment method designed to limit intimal ingrowth.

DeLaria et al. [8], above, (Baxter sponsored) describe in vitro mechanical experience with a glutaraldehyde-fixed bovine jugular vein. Quijano et al. [13, 14], disclose stents and other implantation devices for use with prosthetic valve grafts, such as preserved valve-containing vein segments. A drawback of the disclosed prosthesis is that it includes a mechanical device to connect and restrain vessels and to enclose a glutaraldehyde valve.

With the exception of Hill et al. [2], most attempts to fabricate venous valves were based on the design and materials proven appropriate for heart valves. Heart valves open and close 60 to 150 times per minute with pressures of up to 250 mm Hg. On the other hand, venous valves typically remain open with minimal forward flow and close with flow reversal. Reverse venous flow may develop intermittent pressures of 150 mm Hg.

Therefore, there exists a need in the art for an improved artificial venous valvular prosthetic device that overcomes the above-referenced problems and others.

SUMMARY OF THE INVENTION

In a first aspect of the present invention, a venous valve prosthesis includes a hollow conduit defining a central passageway through which blood may flow. Opposing, pliable leaflet members are located within the conduit and move back and forth between a first, open position, whereby blood may flow through the central passageway in a first direction, and a second, closed position, whereby blood is prevented from backflowing through the central passageway in a second direction which is opposite the first direction. A hollow and generally cylindrical support member retains the leaflet members and is coaxially disposed within the conduit. The support member includes opposing cutaway regions defining two axially extending struts supporting the leaflet members. The cutaway regions, in cooperation with the struts, allow the leaflet members to collapse inwardly to the closed position.

In a second aspect, a method of implanting a prosthetic valve apparatus within a blood vein includes providing a prosthetic valve apparatus as described above. An opening is formed in a blood vessel and the prosthetic valve apparatus is inserted through the formed opening to a desired location. The apparatus is oriented coaxially within the vein such that the leaflet members and struts extend in the direction of forward blood flow. The prosthetic valve apparatus is anchored in the desired position.

In a third aspect, a method of making a venous valve prosthesis includes fastening pliable leaflets to a hollow and generally cylindrical support member including opposing cutaway regions defining two axially extending struts to form a valve subassembly. The leaflets overlie the cutaway regions, are supported by the struts, and are configured to move back and forth between a first, open position, whereby blood may flow through the central passageway in a first direction, and a second, closed position, whereby blood is prevented from backflowing through the central passageway in a second direction which is opposite the first direction. The cutaway regions in cooperation with the struts are configured to allow the leaflet members to collapse inwardly to the closed position. The valve subassembly is coaxially affixed within a hollow conduit defining a central passageway through which blood may flow. In addition, the valve is entirely made from synthetic material and will normally be in an open position. It will only close when a backward flow of blood or a reduced pressure is detected in the vein.

In a fourth aspect, a method of treating valvular insufficiency in a patient suffering therefrom is provided, wherein a prosthetic valve apparatus is inserted into a vein of the patient at a first location selected to restore a valve function in the vein. The prosthetic valve includes a support body of synthetic material and of generally cylindrical shape having a lower circumferential base portion, and opposing cutaway regions defining opposing and axially extending struts. The valve further includes two opposing flexible valve cusps of synthetic material secured to the support body opening and closing the valve, the valve cusps and cutaway regions being dimensioned such that the valve cusps are collapsible against each other to a closed position. A hollow conduit of synthetic material encloses the support body and flexible valve cusps.

One advantage of the present invention resides in that the subject implantable device can be used to restore native valve function in patients who suffer chronic venous insufficiency, e.g., in the form of venous ulcers and/or varicose veins, or venous insufficiency following an episode of deep venous thrombosis (DVT), vascular injury, or venous dilation.

Another advantage of the present valve prosthesis is that it is constructed entirely from synthetic or nonbiological materials.

Another advantage of the present device is that it duplicates the function, although not the form, of the native vein valve.

Still another advantage of the present device is that a designed washing action is provided to insure clearing of all blood contact surfaces with each reversal of blood flow.

Yet another advantage is found in that surface treatment of the device can be provided to enhance bio- and blood compatibility.

Another advantage of the present invention is that it can be implanted surgically or percutaneously via a catheter, and can be implanted at any valve station (level of damaged or destroyed native venous valve) in the deep or superficial venous circulation of the leg.

Still another advantage resides in that internal structures are configured to present a smooth surface to support laminar flow.

Still further benefits and advantages of the present invention will become apparent to those skilled in the art upon a reading and understanding of the preferred embodiments.

BRIEF DESCRIPTION OF THE DRAWINGS

The accompanying drawings, which are incorporated in and constitute a part of the specification, illustrate embodiments of the invention and, together with the description of the invention herein, serve to explain the principles of the invention.

DETAILED DESCRIPTION OF THE PREFERRED EMBODIMENTS

It is to be understood that both the foregoing general description and the following detailed description are exemplary and explanatory only and are not restrictive of the invention as claimed.

The present development is directed to a prosthetic vein valve for implantation within a blood vein or vascular graft, e.g., to replace a diseased or malfunctioning valve. The valve is made from synthetic material, preferably a polymeric material. The valvular prosthesis includes leaflets mounted on a support and positioned within a conduit, all of which cooperate to permit blood flow in one direction only. The leaflets will normally be in an open position, permitting blood to flow through the vein. The leaflets will close, blocking the flow of blood when blood begins to backflow in a direction opposite from its normal flow.

The implantable venous valve prosthetic device of the present invention is particularly suited to restore physiologic blood flow to the human leg in those patients who suffer the insult of chronic venous insufficiency, e.g., in the form of venous stasis ulcers, varicose veins, and so forth. The device is implanted surgically under direct vision to restore valve function to the deep venous circulation to heal venous ulcers, or alternately, can be adapted for implantation using a minimally invasive percutaneous delivery system for venous ulcers as well as varicose veins.

Figure 1:
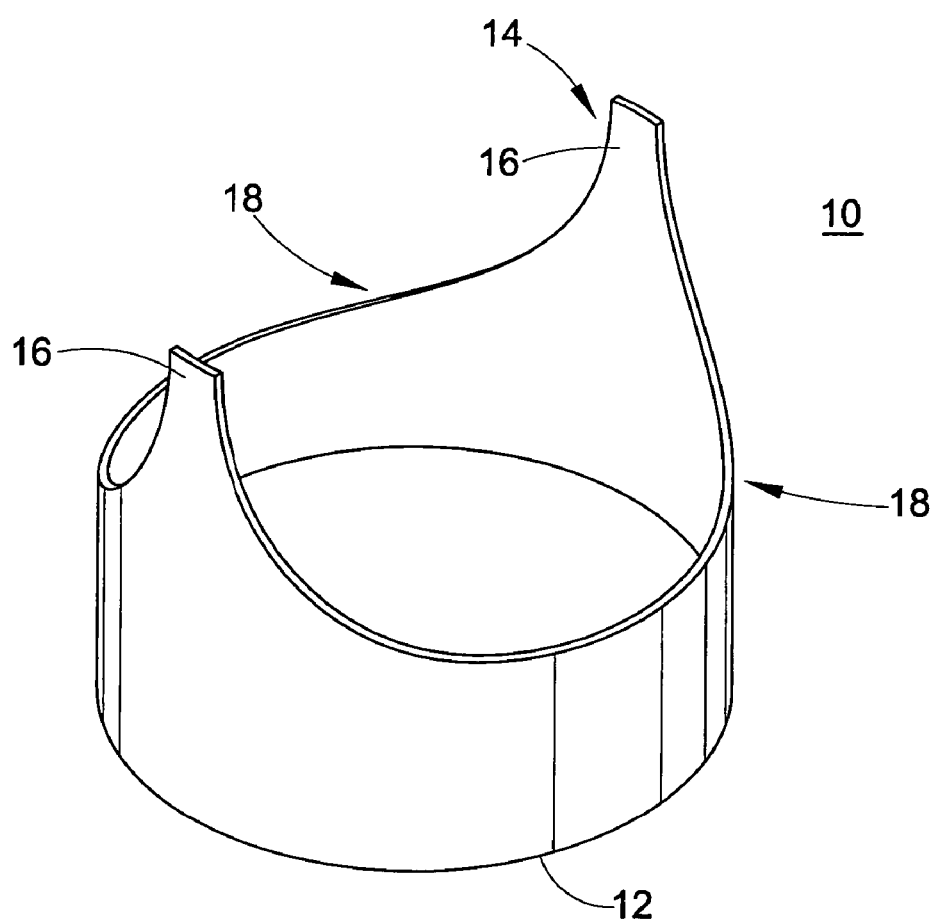
FIG. 1 is a perspective view of a support body in accordance with a first embodiment of the present invention.

Referring to FIG. 1, a support body or stent 10 is formed from a rigid synthetic plastic material, such as molded aromatic urethane. The support body 10 has a hollow, generally cylindrical form with substantially the same diameter throughout. A lower annular portion 12 constitutes an inlet end for the valve. An upper portion 14 includes two opposing, tapered, longitudinally running projections or legs 16 defined by opposing curved cutaway regions 18. The support body 10 can be formed by a number of methods, for example, via an injection molding process, from cut-tubular stock, and so forth.

Figure 2:
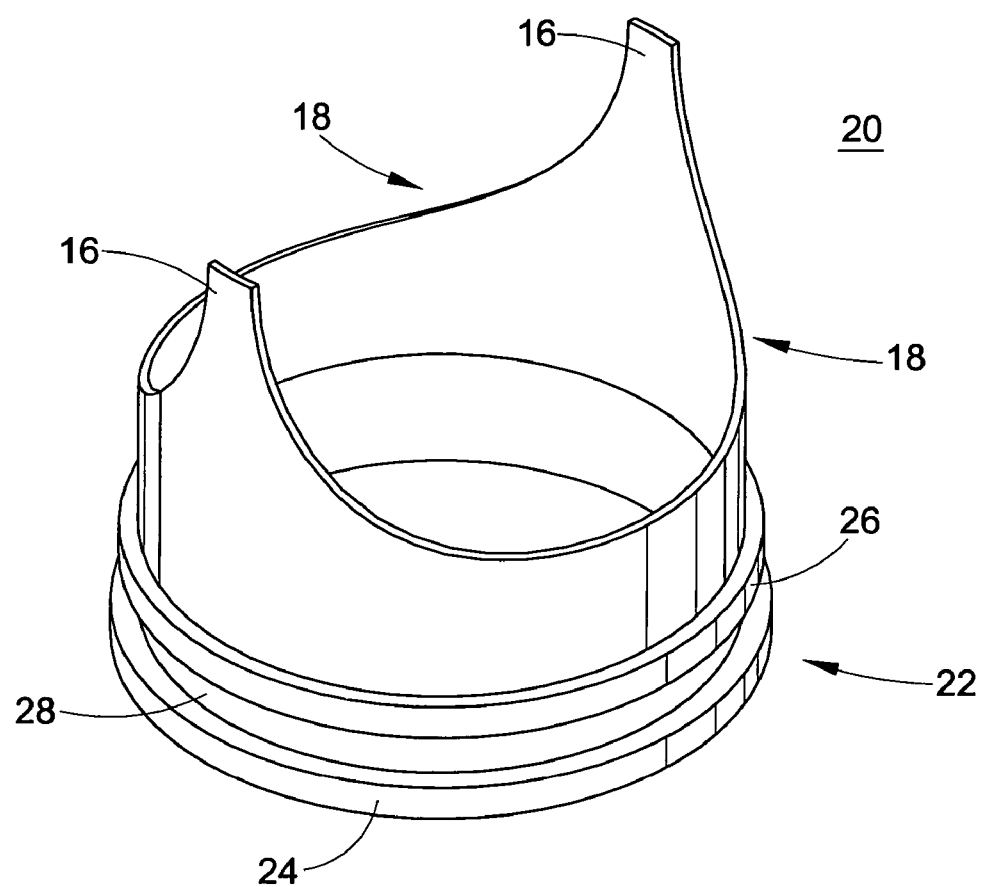
FIG. 2 is a perspective view of a support body in accordance with a second embodiment of the present invention.

Referring now to FIG. 2, a valve support body 20 according to a second embodiment includes a base portion 22 including an attachment means thereon. The base portion 22 includes a flange 24 and an annular raised lip or ridge 26 spaced apart from the flange in the axial direction, thereby defining an annular channel or recess 28 therebetween. The flange 24 and ridge 26 are preferably integrally formed with the support body 20, although separately formed and attached members are also contemplated. In use, the base portion 22 cooperates with an externally applied circumferential ligature placed about the vein or graft containing the valve assembly in axial alignment with the channel 28 to anchor the valve assembly in place and to prevent blood flow around the valve assembly.

Figure 3:
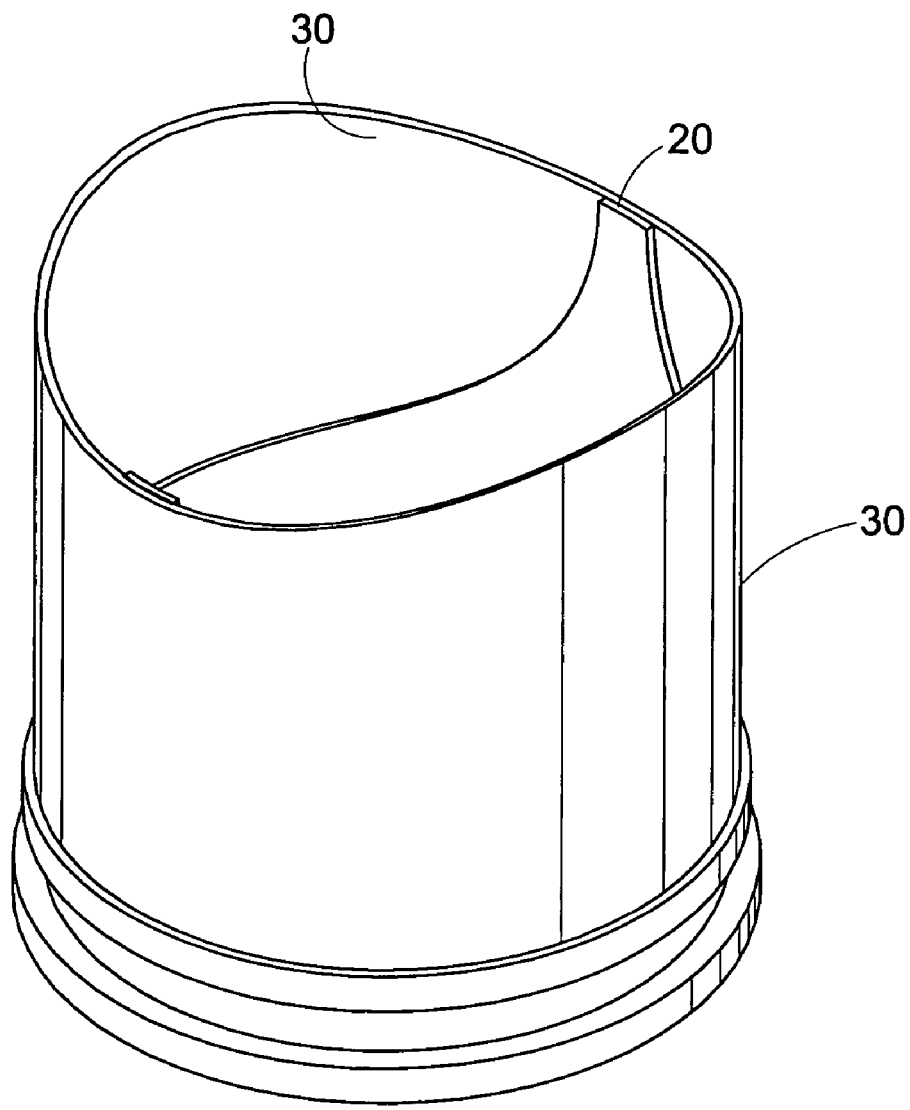
FIG. 3 is a perspective view of a vein valve of the present invention in the open position.
Figure 4:
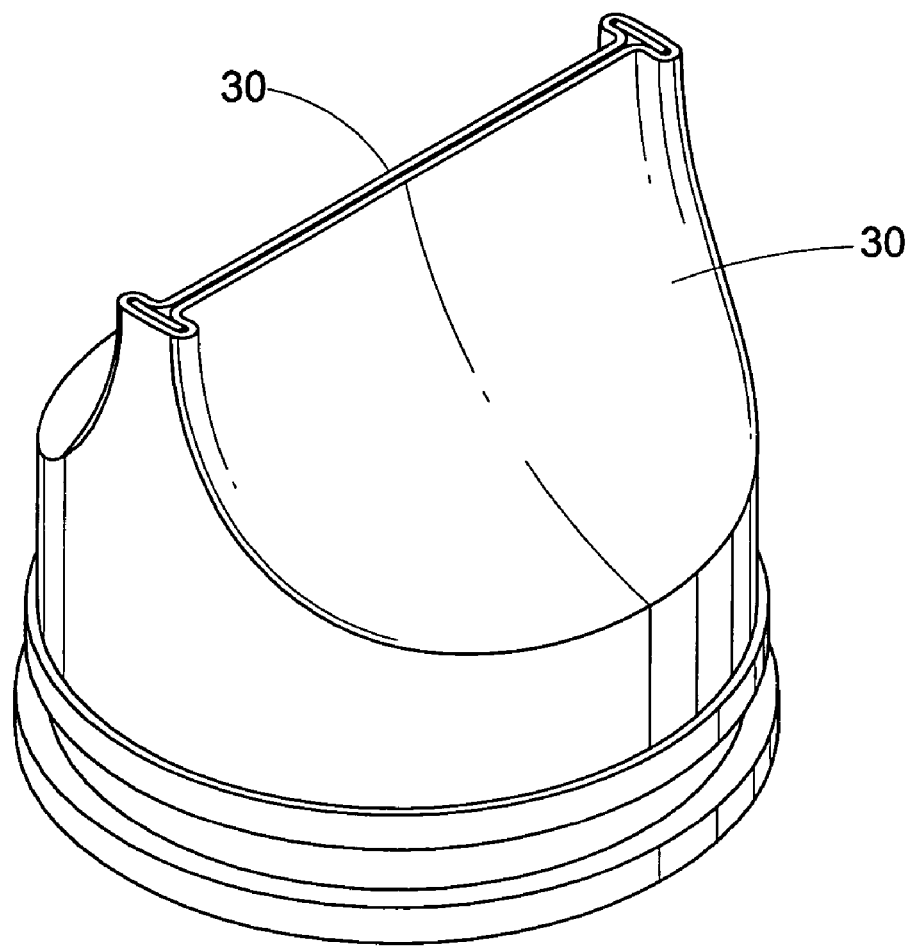
FIG. 4 is a perspective view of the embodiment shown in FIG. 3, in the closed position.

Referring now to FIGS. 3 and 4, a pair of opposing, pliable leaflets, cusps or flaps 30 are fastened to the support body 20, extending over the cutaway regions 18. As used herein, the terms leaflets, flaps and cusps will be used interchangeably to refer to these members. The flaps 30 are formed from a polymeric film, preferably an aromatic urethane film. In the illustrated embodiment, the flaps 30 are formed from a generally tubular film material fastened coaxially to the support body. The leaflets can be blown into a round or tube form in a one- or two-piece configuration conforming to the support body 20. In alternative embodiments, the flaps 30 comprise two separately formed leaflets, for example, cut to shape from a film material, each attached, e.g., via an adhesive, to the support body 20.

The leaflets 30 are attached to the support body 20 using an adhesive, such as a UV cured adhesive. Alternatively, the leaflets 30 are formed integrally with the support body 20.

The leaflets 30 move back and forth between open and closed positions in response to hemodynamic movement. In the open position, illustrated in FIG. 3, the leaflets constitute an outlet through which blood may flow in the forward direction. In the closed position, illustrated in FIG. 4, blood is prevented from backflowing through the valve in the reverse direction. The leaflets are normally in an open position and will only close upon a reverse in blood flow direction. This is in contrast to prior art mechanical valves, which typically operate in both closed and open position during normal blood flow.

The leaflets remain in an open configuration such that blood may flow through the valve in the forward direction. On application of reverse pressure, the cutaway regions 18 in the support 20, in cooperation with the struts 16, allow opposing walls of the leaflets 30 to be depressed or collapsed inwardly together and around the extending projections 16 of the support body. The opposing walls of the leaflets 30 engage each other to provide a seal therebetween, thus preventing blood flow in the reverse direction.

The implantable venous valve device of the subject invention is unique in that it does not attempt to mimic the form of native vein valves, but rather, replaces the function of native vein valve. Again, as with a native vein valve, the normal position of the subject valve is open, and remains open to blood flow toward the heart, i.e., the central venous circulation, and closes upon detection of minimal reverse flow, preferably as little as 3 mm Hg, most preferably 1 mm Hg or less. Such reverse flow situations occur, for example, when a person rises from the supine to upright position; when forward blood flow from the deep circulation is reflected on the superficial venous circulation, such as is the case at the saphenous-femoral junction; and during respiration and/or exertion.

During forward or no blood flow states, the valve leaflets remain open or gently "flutter" with flow. During reverse flow, the valve must close abruptly, stopping all blood flow. The valve should remain competent over a range of about 20 to 200 mm Hg.

Figure 12:
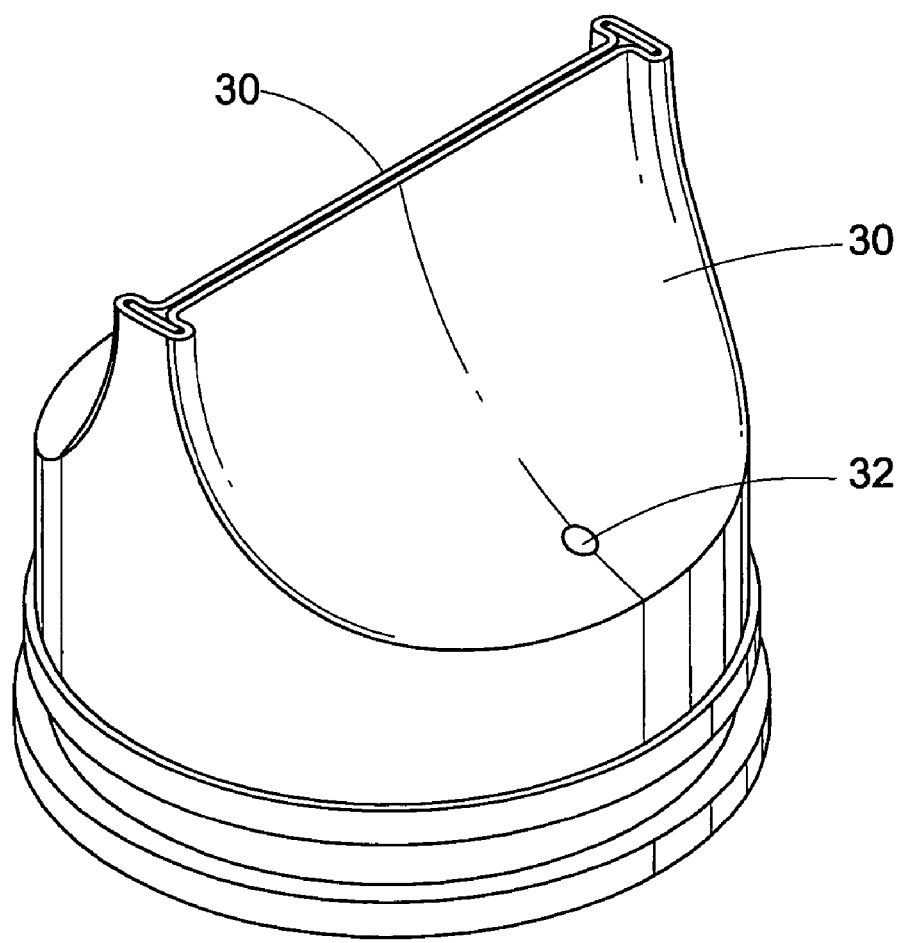
FIG. 12 is a perspective view of an alternate embodiment of a vein valve in accordance with the present invention.

An alternative embodiment may be used to mitigate the effects of the reverse flow associated with a change from a sitting to a standing position. In this configuration, shown in FIG. 12, a small opening 32 is created in at least one of the leaflets 30 at a point where the leaflet extends over the cutaway regions of the support body such that reverse blood flow is slowed, but not completely stopped when the patient changes posture abruptly and the valve leaflets close. This modification helps to maintain blood volume while quickly responding to abrupt flow direction changes. Such an arrangement effectively acts as a "shock absorber", helping to reduce pressure shock to the valve leaflets while minimizing blood pooling in the extremities.

In an alternative embodiment, the leaflets and support body are formed, molded, blown, etc., as one piece consisting of material of graduated thickness to include both the leaflets and an integrally formed support structure.

Figure 5:
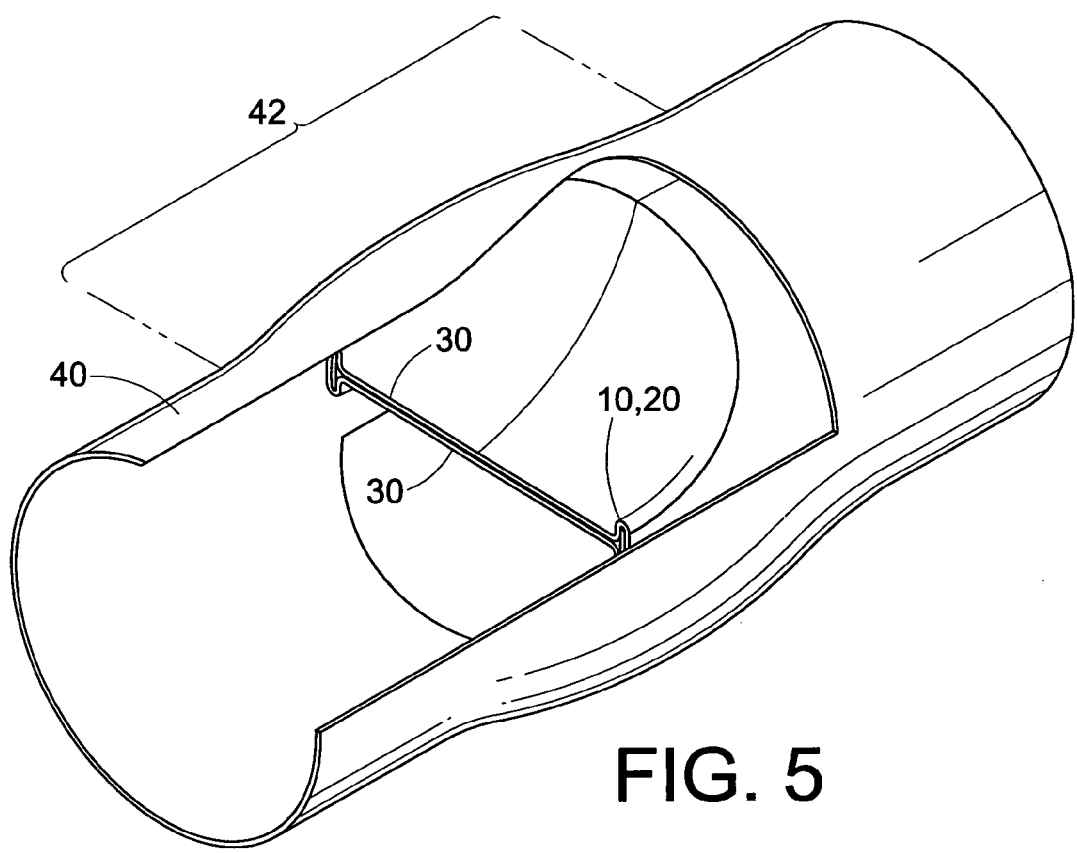
FIG. 5 is a perspective and partial fragmentary view of the subject invention, illustrating an embodiment including a conduit having a bulbous sinus formed therein.

Referring now to FIG. 5, the subassembly comprising the support structure (10, 20) and leaflets 30 is placed within a hollow, cylindrical conduit 40. The conduit 40 is formed, e.g., cut to length, from a known or conventional vascular graft material, preferably expanded PTFE (ePTFE) vascular graft material.

An optional bulbous sinus region 42 is provided in the conduit adjacent the leaflets to facilitate leaflet closure upon pressure reversal. The optional valve sinus can either be formed in the base conduit material (e.g., molded or blown into the inner surface of the conduit), or, via stent dilation of the base conduit. Suture loops, rings, tabs, or the like (not shown) are optionally provided on the conduit for surgical implantation, although percutaneous implantation of the valve device is also contemplated. The optional suture loops, rings, tabs, etc., for vascular attachment can be integral to the outer surface of the conduit (e.g., formed in the same molding process or in a comolding process), or, can be separately formed and attached, e.g., using an adhesive, to the outer surface of the conduit.

The strut/leaflet assembly is preferably attached within the conduit using an adhesive. Alternatively, the strut/leaflet assembly is molded or comolded into the conduit. For example, the conduit can be formed in a two-part process that further incorporates the struts, leaflets, and optional suture loops.

Figure 6:
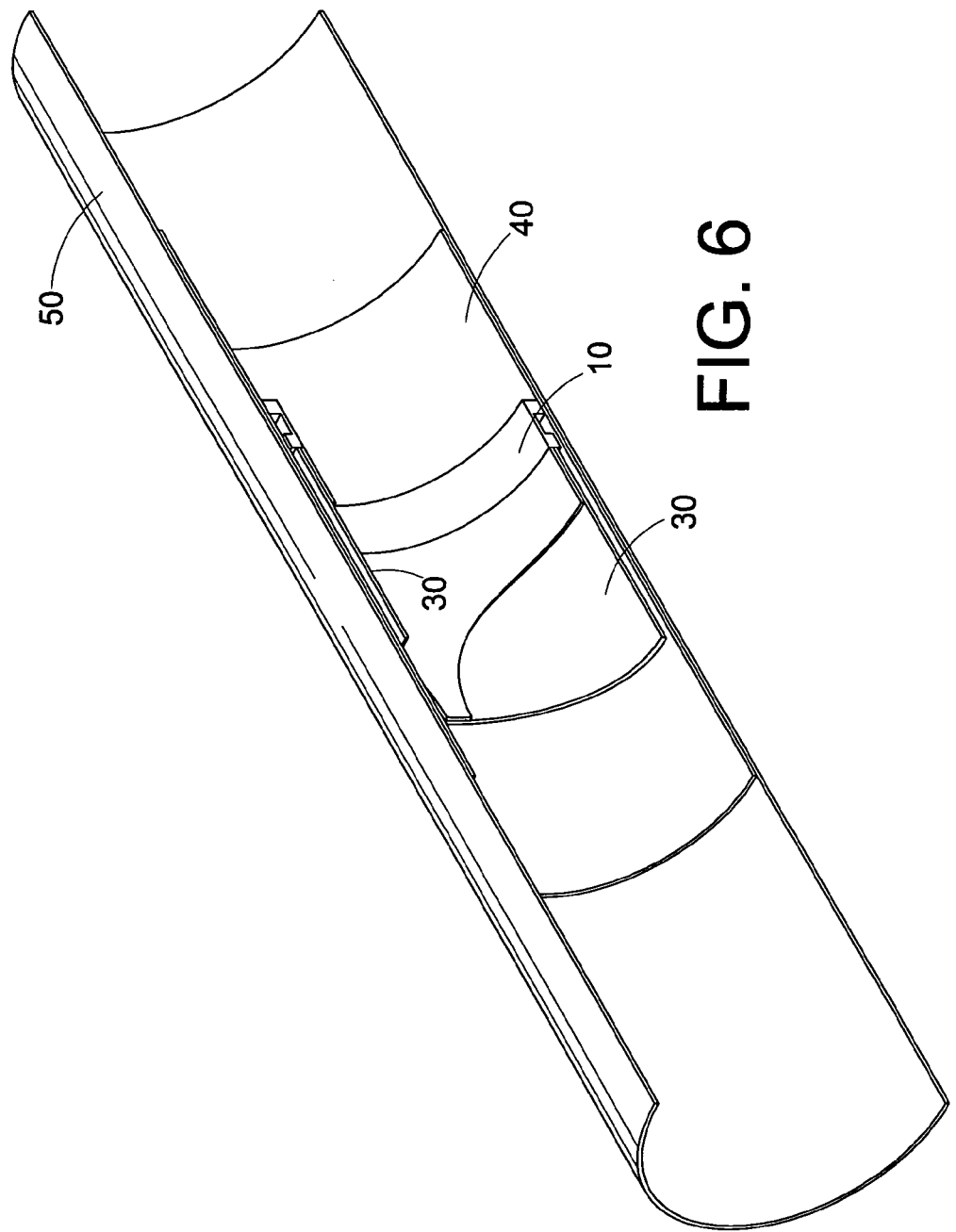
FIG. 6 is an isometric sectional view of the subject valve device in open position in a vein.
Figure 7:
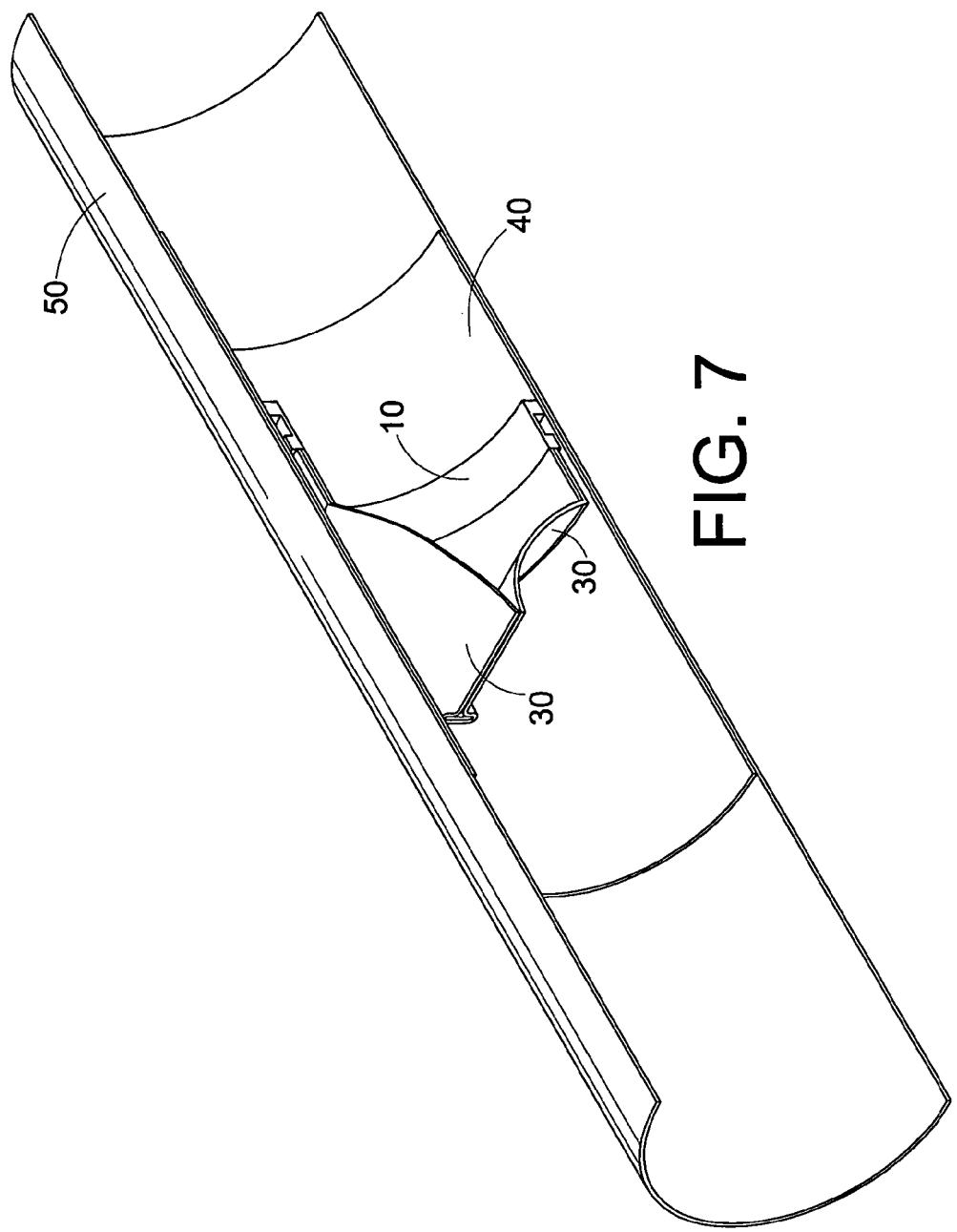
FIG. 7 is an isometric sectional view of the subject valve device in closed position in a vein.

Referring now to FIGS. 6 and 7, the valve replacement device comprising the support body 10, the leaflets 30, and conduit 40 is shown in a vessel 50 in the open and closed position, respectively. The valve device may be either: (1) placed into vessel under direct vision by traditional suturing methods, (2) percutaneously placed in a conduit without a stent, or (3) percutaneously placed with stent dilatation.

Preferably, a washing action takes place with all flow states. On forward flow, flow washes the distal valve and conduit surfaces. On initiation of reverse flow, blood is channeled via the sinus to wash the proximal leaflet surfaces.

When the valve is experiencing forward flow, the internal structures must present a smooth surface to support laminar flow. Turbulence could result in blood clots that may obstruct valve mechanism and/or occlude flow. During reverse flow, the valve closure blood is channeled over the back side of the leaflets and the transition between the conduit and strut/leaflet assembly to remove all static blood remaining to avoid clot formation and embolization.

In a preferred embodiment, the exterior of the conduit is preferably intersticed to allow tissue ingrowth for long-term stability with a seal against blood bypassing the device. The exterior of the conduit may, thus, comprise a mesh material or a material having a porous surface, such as an ePTFE material having pores or other open spaces of a sufficient size to promote tissue ingrowth, as would be understood by those skilled in the art. In a preferred embodiment, ePTFE having a pore size of about 10-100 microns is used.

The internal walls can be formed of a material or coating having a smooth surface to prevent unwanted closure of the passageway due to tissue ingrowth. In a preferred embodiment, the interior surface of the conduit is configured to encourage controlled tissue ingrowth to support laminar flow and a non-thrombogenic blood interface. For example, the interior surface may be formed of a material which promotes controlled tissue ingrowth, such as a polymer impregnated with a biologically responsive chemical.

The boundaries of the conduit are configured to form a transition that discourages the development of intimal hyperplasia that could invade the mechanism of the device.

A suture system may be used to secure the device in place during the period immediately following implant to allow tissue ingrowth in the outer conduit surface. The sutures stabilize position as well as prevent blood from bypassing the device.

The implantable valve device of the present invention can be implanted at any valve station (level of damaged or destroyed native venous valve) in the deep or superficial venous circulation of the leg. The valve device can be implanted surgically under direct vision or, alternatively, inserted into a vein and advanced percutaneously to the desired location.

For surgical implantation, a vein containing damaged native valve or a vein where valve replacement will restore physiologic blood flow is surgically exposed. A longitudinal venotomy of adequate length to accommodate positioning of the device is made at the intended implant site. The length of the incision should be shorter than the longitudinal or axial length of the device. The subject replacement valve is maneuvered into the vein and positioned so that the ends of the device extend beyond the borders of the incision. This keeps the venotomy healing process distant from the device openings. Anchor sutures, placed through the vein wall and suture loops, are secured. A circumferential ligature is placed to prevent blood from flowing around the device when the vessel dilates. The valve is primed with blood and air is eliminated from the vessel before closing the venotomy and the adequacy of repair is demonstrated by "milking" the vessel to demonstrate the freedom of forward blood flow and valve competency when reverse flow is attempted. The surgical incision is closed in the traditional manner.

Figure 8:
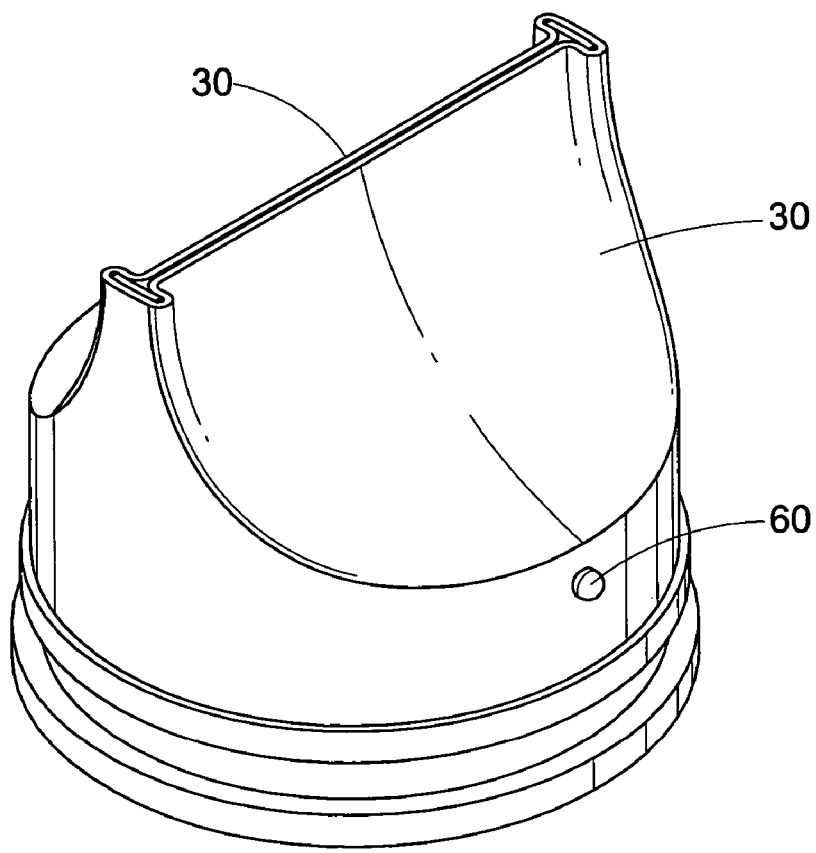
FIG. 8 is perspective view of a vein valve in a closed position having retaining nibs for use with a stent in accordance with another embodiment of the present invention.

The valve device can also be implanted using a stent and balloon catheter assembly. In this implantation method, the valve subassembly comprising the support structure and leaflets and a metal or plastic stent are placed over a balloon catheter. As shown in FIG. 8, the vein valve is preferably equipped with one or more polymeric nibs 60 preferably positioned on the support structure 20 or on the leaflets 30 where the leaflets overlay the lower annular portion of the support structure just below the cutaway regions. The nibs may be conical, hemispherical or any other convenient shape. The valve structure is preferably molded with the nibs 60, although the nibs may be added after the molding of the valve using an adhesive.

Figure 9:
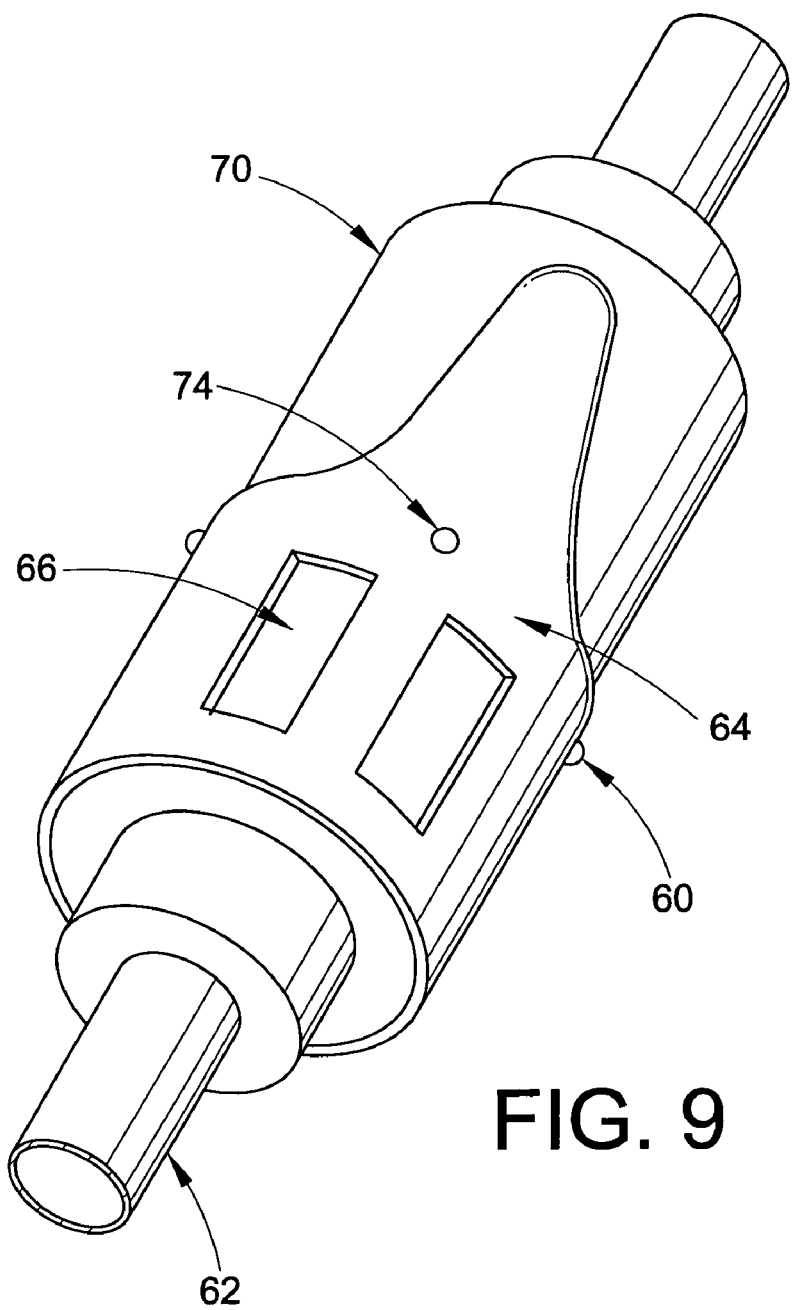
FIG. 9 is a perspective view of a vein valve in accordance with the present invention mounted on an uninflated balloon catheter with an outer stent.
Figure 10:
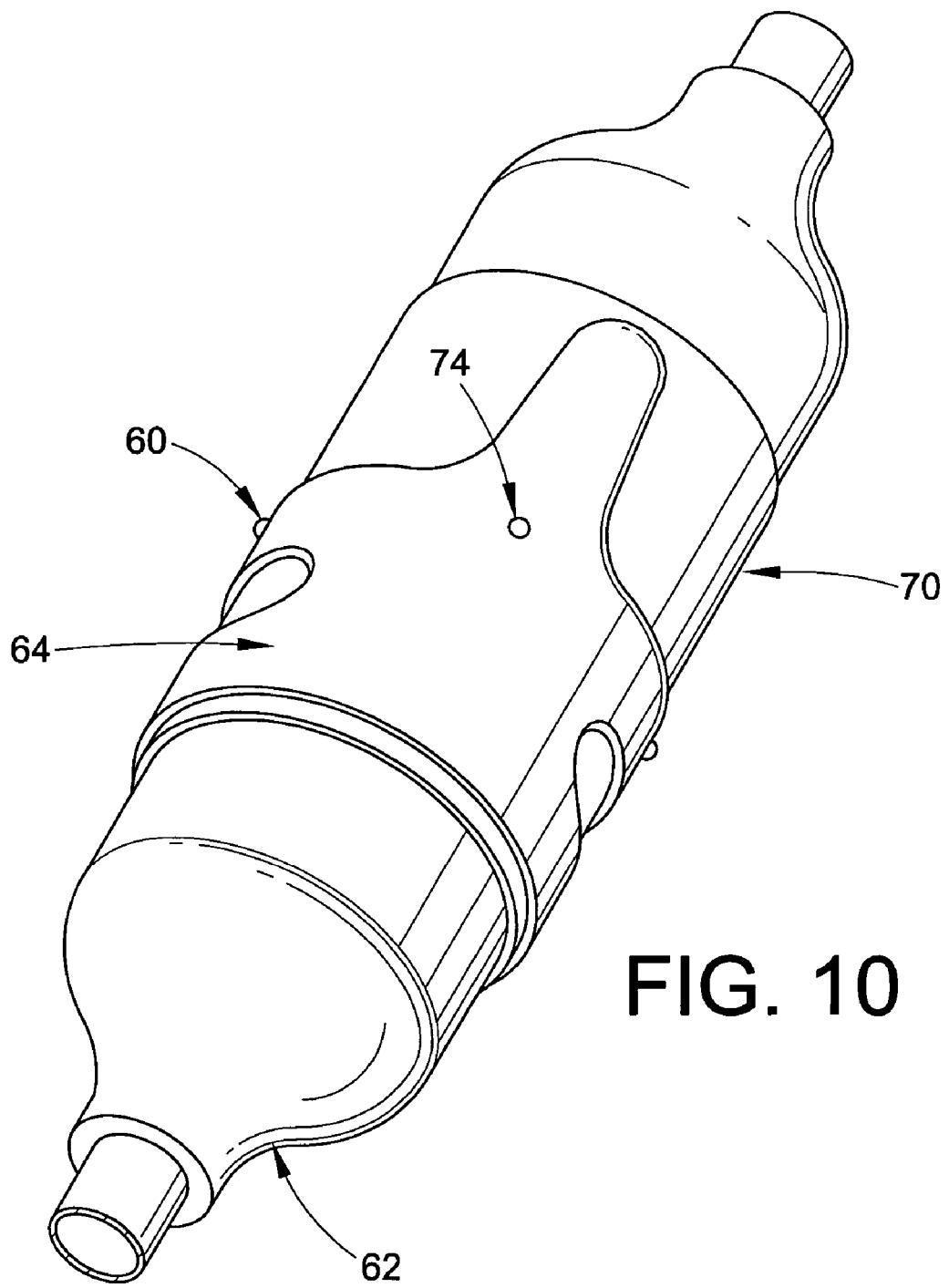
FIG. 10 is a perspective view of the embodiment shown in FIG. 9 with the balloon catheter inflated.

With reference to FIGS. 9 and 10, the valve assembly 70 comprising the support body and the leaflets 30 is placed over a deflated balloon catheter 62 and a plastic or metal stent 64 is placed over and around the valve assembly. The stent 64 may be a tubular member having a mesh structure and/or equipped with apertures 66 defined on and extending through its outer surface. A plurality of barbs 74 may be disposed on the stent's outer surface. The valve assembly 70 is placed within the stent such that the nibs 60 line up and project through apertures 66 defined on the stent 64. These nibs 60 secure the valve assembly 70 to the stent as well as establish a buffer between the stent and the valve assembly, preventing the stent from wearing on the leaflets 30 at a point where the leaflets are attached to the support body 20, when the valve/stent assembly is deployed in a vein.

The catheter 62 with the valve assembly 70 and stent 64 is introduced into the in vivo site vessel from a distal location to the desired site of placement and advanced along the vein in a conventional manner. Once at the correct location in the leg vessel, the balloon feature of the catheter is inflated and the venous valve/stent assembly is distended into the vessel lumen. With the venous valve/stent assembly distended and deployed and the balloon catheter still inflated, the entire configuration is rotated to place the stent barbs 74 into the vessel wall, thus locking the valve/stent assembly in place. The catheter is then removed, leaving the stent 64 and valve assembly 70 in place. Both the valve and the stent may be coated with one or more drugs to enhance the valve durability and to prevent clotting.

In this embodiment, the stent can actually act as the valve conduit 40 described with reference to FIGS. 5-7 in the embodiments above. Alternately, a separate valve conduit can be placed in the vein prior to or concurrently with the deployment of the stent and valve assembly.

Figure 11:
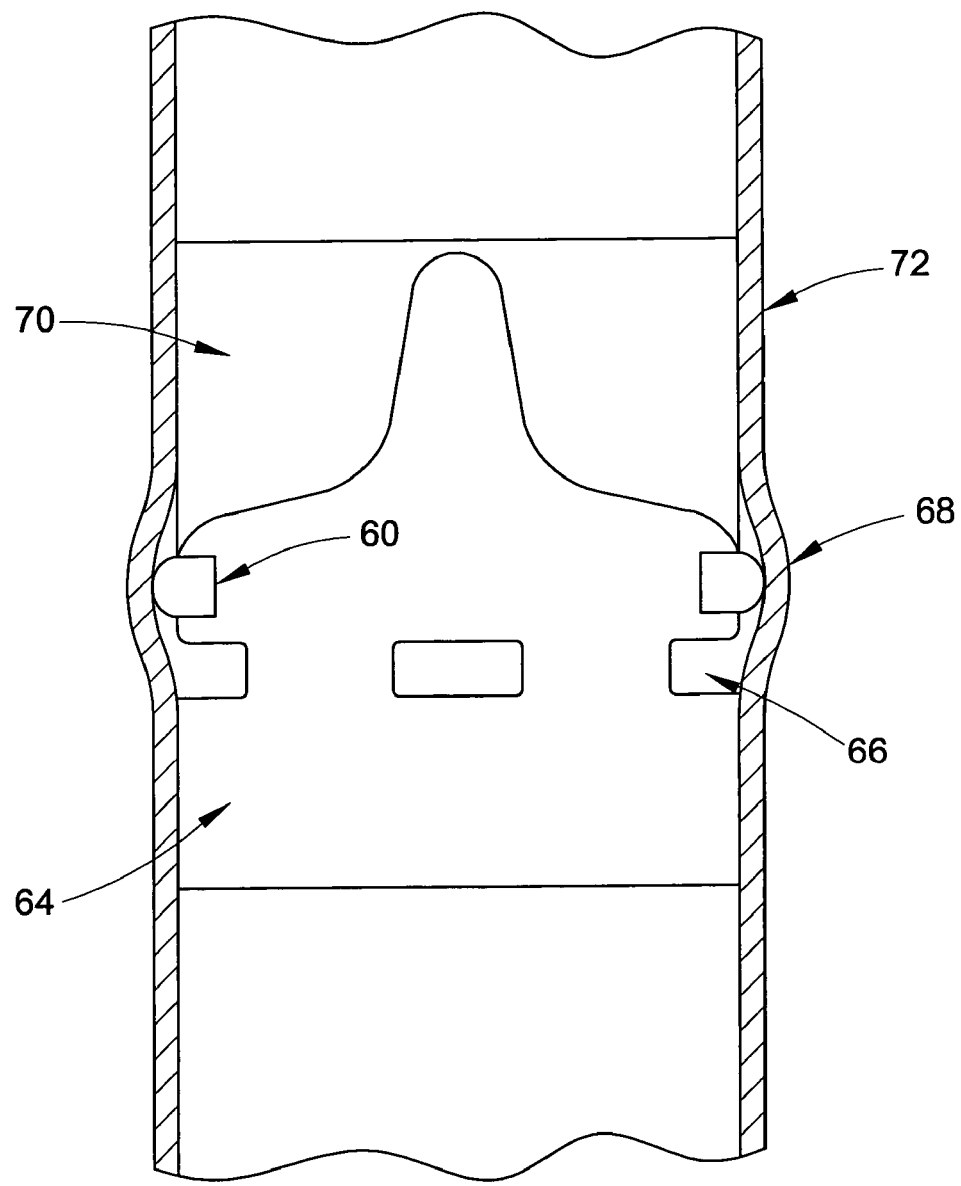
FIG. 11 is a side view of the stent and vein valve implanted in a vein.
Figure 13:
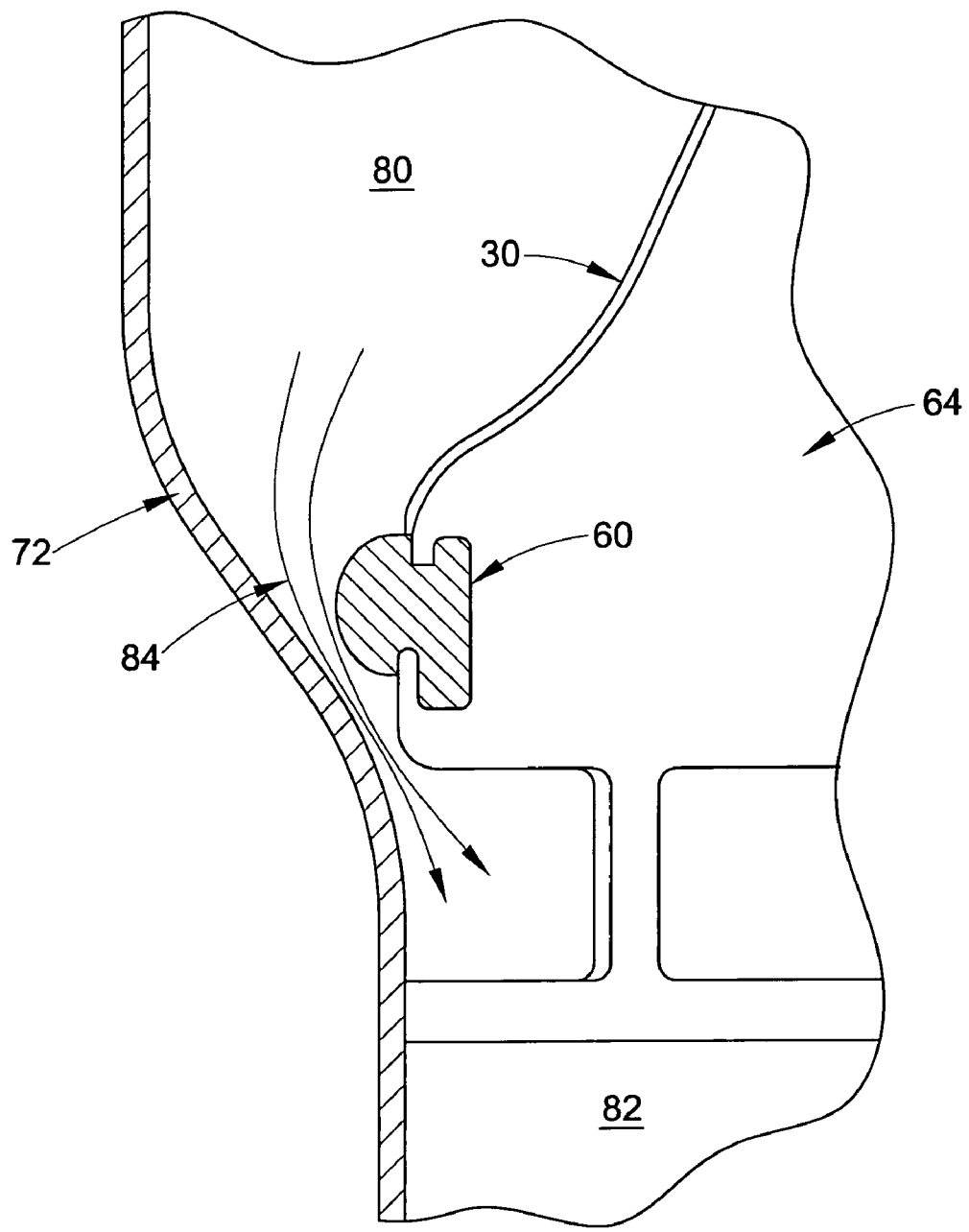
FIG. 13 is a magnified view of a portion of the embodiment shown in FIG. 11.

With reference to FIGS. 11 and 13, in addition to establishing a buffer between the stent 64 and the valve assembly 70 as described above, the nibs 60 protruding through the stent create a slight bulge 68 in the vessel wall 72. This slight bulge 68 creates a small leak path 84 when the leaflets 30 are closed from the positive pressure side 80 of the valve to the low or negative pressure side 82 of the valve. This leak path 84 creates a washing effect on the leaflet by the backflow of blood from the high pressure side 80 to the low pressure side 82, as described above. The leak 84 also performs a similar function to the small opening in the leaflet base in one of the embodiments of the valve described above, allowing a small amount of blood to flow past the valve when it is closed, helping to maintain blood volume as well as reducing blood pooling and pressure shock to the valve leaflets and allowing the valve to quickly respond to abrupt changes in flow direction.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

REFERENCES

All references cited herein are incorporated by reference in their entireties.

[1] Criado et al., "Venous disease," *Current Problems in Surgery*, Vol. 28, No. 5, pp. 335-400 (May 1991).
[2] Hill et al., "Development of a prosthetic venous valve," *Journal of Biomedical Materials Research*, Vol. 19, No. 7, pp. 827-32 (September 1985).
[3] Van Bemmelen et al., "The mechanism of venous valve closure. Its relationship to the velocity of reverse flow," *Archives of Surgery*, Vol. 125, No. 5, pp. 617-19 (May 1990).
[4] Van Cleef, "A vein has a preferential axis of flattening," *The Journal of Dermatologic Surgery and Oncology*, Vol. 19, No. 5, pp. 468-70 (May 1993).
[5] Taheri et al., "Experimental prosthetic vein valve," *The American Journal of Surgery*, Vol. 156, No. 2, pp. 111-14 (August 1988).
[6] Taheri, U.S. Pat. No. 4,851,001, issued Jul. 25, 1989.
[7] Taheri et al., "Experimental prosthetic vein valve. Long-term results," *AngiograDhy*, Vol. 46, No. 4, pp. 299-303 (April 1995).
[8] DeLaria et al., "Hemodynamic evaluation of a bioprosthetic venous prosthesis," *Journal of Vascular Surgery*, Vol. 18, No. 4, pp. 577-86 (October 1993).

[9] Reeves et al., "Mechanical characteristics of lyophilized human saphenous vein valves," *Journal of Vascular Surgery*, Vol. 26, No. 5, pp. 823-28 (November 1997).

[10] Burkhart et al., "Experimental repair of venous valvular insufficiency using a cryopreserved venous valve allograft aided by a distal arteriovenous fistula," *Journal of Vascular Surgery*, Vol. 26, No. 5, pp. 817-22 (November 1997).

[11] Dalsing et al., "A multicenter, phase I evaluation of cryopreserved venous valve allografts for the treatment of chronic deep venous insufficiency," *Journal of Vascular Surgery*, Vol. 30, No. 5, pp. 854-64 (November 1999).

[12] Kumins et al., "Free tissue transfer provides durable treatment for large nonhealing venous ulcers," *Journal of Vascular Surgery*, Vol. 32, No. 5, pp. 848-54 (November 2000).

[13] Quijano et al., U.S. Pat. No. 5,824,061, issued Oct. 20, 1998.

[14] Quijano et al., U.S. Pat. No. 5,500,014, issued Mar. 19, 1996.

What is claimed is:

1. A venous valve prosthesis comprising:
    pliable leaflet members configured to move back and forth between an open position allowing blood flow in a forward direction, and a closed position substantially blocking blood backflow;
    a hollow and generally cylindrical support member retaining the leaflet members thereon; and
    an aperture defined in at least one of the leaflet members such that blood may backflow through the aperture when the leaflets are in the closed position, the aperture allowing a small amount of blood to backflow when the valve is in the closed position so that the closed valve cannot completely stop blood flow in the closed position.

2. The venous valve prosthesis as set forth in claim 1, further comprising:
    a surrounding hollow conduit defining a central blood flow passageway, the conduit including an enlarged diameter portion radially encircling said leaflet members.

3. The venous valve prosthesis as set forth in claim 1, further comprising:
    a hollow conduit including a porous exterior surface configured to promote tissue ingrowth.

4. The venous valve prosthesis as set forth in claim 1, further comprising:
    a hollow conduit including an interior surface configured to promote controlled tissue ingrowth.

5. The venous valve prosthesis as set forth in claim 1, wherein the leaflet members are adhesively fastened to the support member.

6. The venous valve prosthesis as set forth in claim 1, wherein the leaflet members are integrally formed with the support member.

7. The venous valve prosthesis as set forth in claim 1, wherein the venous valve prosthesis includes at least one porous exterior surface comprising a mesh material configured to promote controlled tissue ingrowth.

8. The venous valve prosthesis as set forth in claim 1, wherein the venous valve prosthesis includes at least one porous exterior surface having a pore size of about 10-100 microns configured to promote controlled tissue ingrowth.

9. The venous valve prosthesis as set forth in claim 1, wherein the venous valve prosthesis includes at least one internal wall comprising a polymer surface impregnated with a biologically responsive material to promote controlled tissue ingrowth.

10. The venous valve prosthesis as set forth in claim 1, further comprising:
    a hollow conduit defining a central blood flow passageway, the hollow conduit including a bulbous sinus region adjacent the leaflet members.

11. The venous valve prosthesis as set forth in claim 1, wherein the venous valve prosthesis is constructed entirely from synthetic or nonbiological materials.

12. A venous valve prosthesis comprising:
    pliable leaflet members configured to move back and forth between an open position allowing blood flow in a forward direction, and a closed position substantially blocking blood backflow;
    a hollow and generally cylindrical support member retaining the leaflet members thereon; and
    one or more uncovered openings passing through at least one leaflet member.

13. The venous valve prosthesis as set forth in claim 12, wherein the venous valve prosthesis is constructed entirely from synthetic or nonbiological materials.

14. The venous valve prosthesis as set forth in claim 12, wherein the one or more uncovered openings passing through at least one leaflet member cause the pliable leaflet members to slow but not completely stop reverse blood flow in the closed position.

15. A venous valve prosthesis comprising:
    a valve assembly including:
        a hollow support member defining a central blood flow passageway, and
        pliable leaflet members retained by the hollow support member and configured to move back and forth between an open position a closed position substantially blocking the central blood flow passageway;
    wherein the valve assembly is configured to allow venous blood flow in a forward direction through the central blood flow passageway when the pliable leaflet members are in the open position; and
    wherein the valve assembly includes one or more openings passing through at least one of the pliable leaflet members such that the valve assembly slows but not completely stop venous blood flow in a reverse direction through the central blood flow passageway when the pliable leaflet members are in the closed position.

16. The venous valve prosthesis as set forth in claim 15, wherein the venous valve prosthesis is constructed entirely from synthetic or nonbiological materials.

17. The venous valve prosthesis as set forth in claim 15, wherein the one or more openings are uncovered openings.

* * * * *